United States Patent [19]

Gavello

[11] Plant 4,142

[45] Nov. 1, 1977

[54] ESCALLONIA (COMPAKTA) PLANT

[76] Inventor: Louis E. Gavello, 3436 Maricopa Ave., Richmond, Calif. 94804

[21] Appl. No.: 734,371

[22] Filed: Oct. 19, 1976

[51] Int. Cl.[2] ..... A01H 5/00

[52] U.S. Cl. ..... Plt./54

[58] Field of Search ..... Plt./54

*Primary Examiner*—Robert E. Bagwill

[57] ABSTRACT

A new and distinct variety of Escallonia plant characterized by its very compact mounding form, having a low height and spread greater than its height; distinct pink flowers; long blooming period; resistance to weather and disease; and slow growth and controlled habit.

1 Drawing Figure

1

My invention relates to a new and distinct variety of Escallonia which originated in my growing grounds in Richmond, Calif. It was found in an area containing three Escallonia plants from Fort Bragg and one Escallonia seedling grown from one of the above Fort Bragg plants.

The parentage of this new and distinctive variety of Escallonia is unknown to me but appears to be a chance hybrid between an Escallonia from Fort Bragg and a seedling, therefrom.

The new hybrid was discovered in November, 1965 and 40 cuttings were asexually reproduced in June, 1966 in the same growing grounds from medium soft cuttings rooted in a medium course sand. 175 more of such asexual reproductions were made in 1968. Cuttings are now being taken from succeeding generations.

Among the outstanding characteristics of this new variety is the very compact form which it attains. In a period of five years it has grown to a height of 28 inches with a spread of 34 inches.

The accompanying picture shows in separate views, a typical bush of my new variety of Escallonia plant, a number of racemes on a branch, and specimens of individual leaves, all depicted in color as nearly true as it is reasonably possible to make the same in a color illustration of this character.

The following is a detailed description of the new variety, with color terminology in accordance with Maerz and Paul, a Dictionary of Color, 2nd Edition, 1950.

FORM

New shrub grows to a height of approximately 2⅓ feet and a width of approximately 3 feet. It is compact and of upright bush form.

FOLIAGE

Between Cypress and Forest Green as identified by plate 23, L-6 on pages 68 and 69.

Oblanceolate to lance-elliptic, ⅞ to 1¼ inches in length and ⅜ to 9/16 inches in width.

Glabrous, shiny above, dull below.

Leaf margins minutely serrate.

Leaves borne on stout petioles approximately ⅛ inch long.

2

FLOWERS

Pink in color as identified by Plate 49 on pages 120 and 121. The center of the flower pedals is J6. The outer edge of the pedals is shaded from K6 to L6.

Flowers are borne in terminal, moderately compact panicles of approximately 1¾ inches long and 1¼ inches wide with about 20 flowers in each.

Branches of the panicle are subtended by bracts: foliaceous below and smaller in the upper parts.

Individual flowers are on pedicals about ¼ inch long.

Calyx of 5 triangular sepals about 3/16 inch long spreading as the flower opens.

Corolla of 5 pedals about ½ inch long; the claw about ¼ inch long and 1/16 inch wide; the blade ovate to elliptic, about ¼ inch long and ⅛ to 3/16 inch wide.

Anthers and style barely exserted; anthers 5 in number, greenish with yellow pollen; base of style surrounded by a yellowish gland.

BLOOMING PERIOD

In the San Francisco Bay Area the plant has a blooming period from July until September.

WEATHER RESISTANCE

The plant grows best in full sun but does well in partly shaded area. It has withstood cold weather of 20° above zero.

DISEASE RESISTANCE

The plant is free of major diseases.

Having described and illustrated my new variety of Escallonia plant, I claim:

1. A new and distinct variety of Escallonia plant, substantially as illustrated and described and characterized as to novelty by:

a. the very compact mounding form of the plant having a low height and spread greater than its height;
b. the distinct pink color of the flowers;
c. the long blooming period;
d. its resistance to weather and disease;
e. its slow growth and controlled habit, making it a very suitable plant for restricted areas.

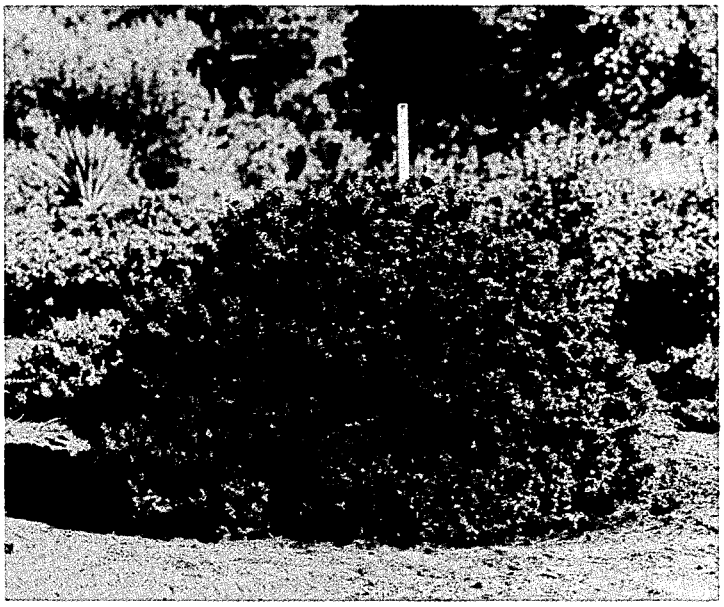
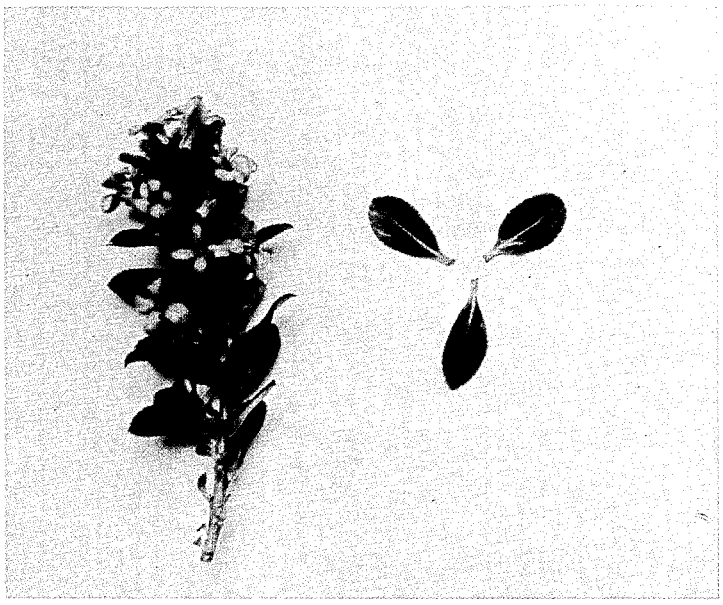

* * * * *